(12) United States Patent
Liebeskind et al.

(10) Patent No.: US 6,441,194 B1
(45) Date of Patent: Aug. 27, 2002

(54) SYNTHESIS OF 4-SUBSTITUTED PYRROLE-2-CARBALDEHYDE COMPOUNDS

(75) Inventors: Lanny S. Liebeskind, Atlanta, GA (US); Wansheng Liu, Plainsboro, NJ (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 09/694,655

(22) Filed: Oct. 23, 2000

Related U.S. Application Data

(60) Provisional application No. 60/160,776, filed on Oct. 21, 1999.

(51) Int. Cl.$^7$ ............................................. C07D 207/32
(52) U.S. Cl. ...................................................... 548/530
(58) Field of Search ........................................ 548/530

(56) References Cited

U.S. PATENT DOCUMENTS 3,998,844 A  12/1976  Carson
4,070,366 A  1/1978  Gregorovich et al.

FOREIGN PATENT DOCUMENTS

WO    WO 00/52012    9/2000

OTHER PUBLICATIONS

Anderson et al Synthesis (1985) 353–363.*
Anderson et al., "Pyrrole Chemistry, V. Friedel Crafts Isopropylations of Some Pyrrole Derivatives,", 1966, Canadian Journal of Chemistry, vol. 44, p. 1831–1839.

Anderson et al., "Pyrrole Chemistry, XIX. Reactions of 2–Pyrrolecarbonitrile and Its 4–Substituted Derivatives," 1978, Canadian Journal of Chemistry, vol. 56, p. 654–7.

Anderson et al., "Pyrrole Chemistry, III. Friedel Crafts Isopropylations of Methyl 2–Pyrroecarboxylate,", 1964, Canadian Journal of Chemistry, vol. 42, p. 1279–87.

Mueller–Westerhoff et al., "Azines and Imines of 4–and 5–t–Bu–Pyrrole–2–aldehyde. A Useful Synthesis of the Aldehydes," 1994, Synthetic Communications vol. 24(10), p. 1389–93.

DeGroot et al., "Mild Preparation of Pyrrole–2–Carboxyaldehydes," 1981, Organic Preparations and Procedures Int. 13(2) p. 97–101.

* cited by examiner

Primary Examiner—Joseph K. McKane
Assistant Examiner—Kamal Saeed
(74) Attorney, Agent, or Firm—Needle & Rosenberg, P.C.

(57) ABSTRACT

The invention relates to an a process for making a 4-substituted pyrrole-2-carbaldehyde compound comprising reacting:

a. a pyrrole-2-carbaldehyde compound; and
b. an alkylating agent;
c. in the presence of at least one catalyst; to form a 4-alkyl substituted pyrrole-2-carbaldehyde compound.

22 Claims, No Drawings

SYNTHESIS OF 4-SUBSTITUTED PYRROLE-2-CARBALDEHYDE COMPOUNDS

CROSS REFERENCE TO RELATED APPLICATIONS

This application claims priority to U.S. provisional patent application serial No. 60/160,776, filed Oct. 21, 1999, which is hereby incorporated herein by reference, in its entirety for all purposes.

ACKNOWLEDGEMENTS

This invention was made with government support under Grants CA40157 awarded by the Department of Health and Human Services, and the National Cancer Institute. The government has certain rights in the invention.

FIELD OF THE INVENTION

This invention relates to methods for selective synthesis of 4-substituted-pyrrole-2-carbaldehyde compounds, via alkylation reactions.

BACKGROUND OF THE INVENTION

Pyrroles are a family of heterocyclic compounds comprising a five-membered ring residue with four carbon atoms, one nitrogen atom, and two carbon-carbon double bonds. A wide variety of substituent groups (designated generally herein as "$S_x$") may be bonded to any of the five atoms of the pyrrole ring. The permissible substituent groups include but are not limited to hydrogen, alkyl groups, aromatic groups, acyl groups, halides, etc. The present invention relates to methods for selectively converting cering an aldehyde substituent at the 2-position of the pyrrole ring) to 4-alkylated-pyrrole-2-carbaldehyde compounds having alkyl residues or groups ("$R_4$") at the 4-position of the pyrrole ring, as shown below. tain pyrrole-2-carbaldehydes (i.e. pyrrole compounds hav

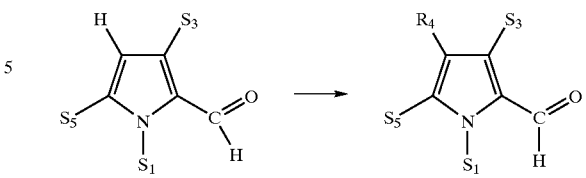

wherein $R_4$ is an alkyl or substituted alkyl substituent having at least four carbon atoms.

As disclosed by Streitweiser and Heathcock (*Introduction to Organic Chemistry*, Macmillan Publishing Co. Inc., New York, 1976, at pages 1080–1088) pyrrole rings may undergo electrophillic substitution reactions analogous to those typical of benzene-type aromatic compounds. For example, pyrroles undergo "Friedel-Crafts" type "alkylation" reactions, in which an alkylating agent (such as an alkyl halide, an alcohol, or an olefin) is reacted with a pyrrole in the presence of a catalyst, which results the removal of a hydrogen from one of the pyrrole carbons, and substitution of an "alkyl" group or residue therefore.

Friedel-Crafts alkylation reactions have been utilized by prior workers to synthesize 4-substituted-pyrrole-2-carbaldehyde compounds. For example, Anderson et.al. (Can. J. Chem. 56, 654–657 (1978)) reacted pyrrole-2-carbonitrile with t-butyl chloride in the presence of aluminum or gallium chloride catalysts, to obtain either 4-t-butyl-pyrrole-2-carbonitrile, or 5-t-butyl-pyrrole-2-carbonitrile. Each of the two isomers of the t-butyl-pyrrole-2-carbonitriles were then reduced to the corresponding aldehydes.

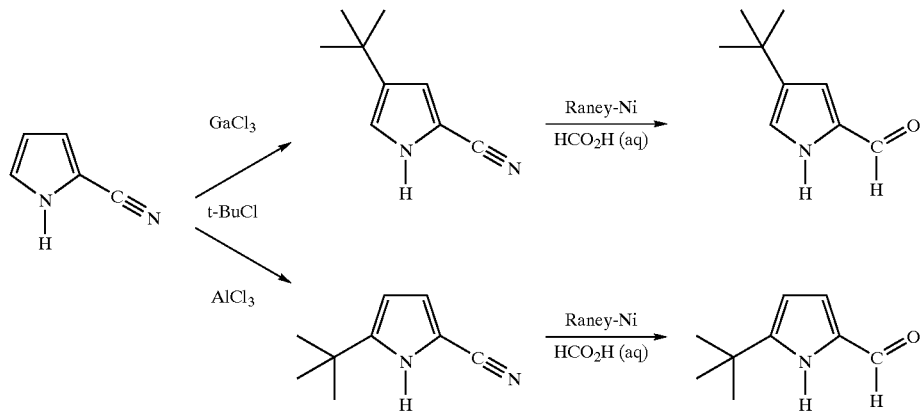

In another approach, Mueller-Westerhoff and Sweigers (Synthetic Communications, 24(10), 1389–1393 (1994)) protected the nitrogen atom of a pyrrole, alkylated in the 4-position with t-butyl chloride/aluminum chloride, depro tected the nitrogen atom, then formulated the 2-position utilizing a Vulsmeir reagent.

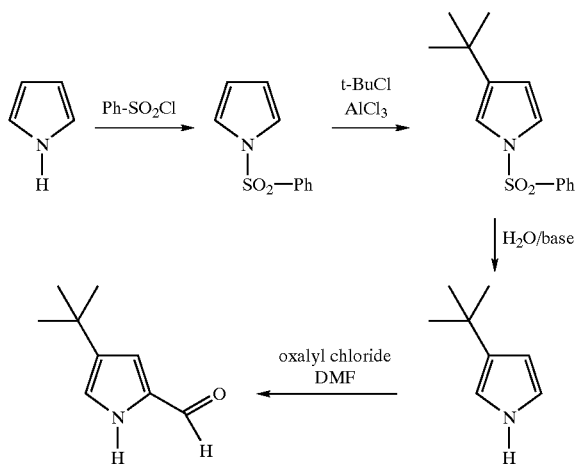

In yet another approach to 4-alkyl-pyrrole-2-carbaldehydes, Anderson et.al.(Can. J. Chem., 44, 1831–1839 (1966)) disclosed selective isopropylation of pyrrole-2-carbaldehyde in the presence of various catalysts to give 4-isopropyl-pyrrole-2-carbaldehyde.

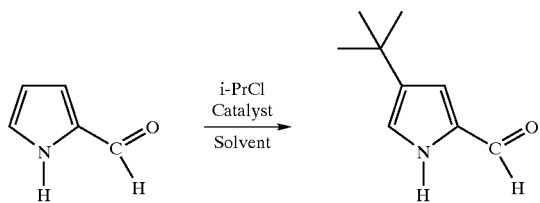

Recently, three United States patent applications, including provisional patent application Serial No. 60/123,058, filed Mar. 5, 1999, provisional patent application Serial No. 60/123,962, filed Mar. 12, 1999, and U.S. utility patent application Ser. No. 09/518,863, filed Mar. 3, 2000 (which are hereby incorporated by reference in their entirety) disclose use for certain classes of 4-alkyl-substituted-pyrrole-2-carbaldehydes, i.e., as intermediates for the synthesis of certain porphyrin compounds.

The 4-alkyl-pyrrole-2-carbaldehydes provided by the current invention can also be used to synthesize various dipyrroles or tripyrroles, which can be intermediates for the synthesis of porphyrins having 4-alkyl substituents, according to the methods described in U.S. patent application Ser. No. 09/524,621, filed Mar. 13, 2000. Additionally, these classes of 4-alkyl-pyrrole-2-carbaldehydes and 4-alkyl-2-hydroxymethyl pyrroles may be valuable intermediates for the synthesis of pharmaceuticals containing heterocyclic residues.

Therefore, there is a need for improved methods and processes for synthesizing 4-alkyl-pyrrole-2- carbaldehydes including, and 4-tertiary-alkyl-pyrrole-2-carbaldehydes.

SUMMARY OF THE INVENTION

The present invention provides improved processes for synthesizing 4-alkyl-pyrrole-2-carbaldehydes, including 4-tertiary-alkyl-pyrrole-2-carbaldehydes. Therefore, this invention, in one aspect, relates to a process for making a 4-alkyl substituted pyrrole-2-carbaldehyde compound comprising reacting:

a. a pyrrole-2-carbaldehyde compound; and
b. an alkylating agent having at least four carbon atoms; in the presence of at least one catalyst; to form a 4-alkyl substituted pyrrole-2-carbaldehyde compound.

The invention further provides a process for making 4-t-butyl-pyrrole-2-carbaldehyde compound comprising:

a. dispersing pyrrole-2-carbaldehyde and from about 1.0 to about 1.5 molar equivalents of $AlCl_3$ in a solvent:
b. adding from about 0.8 to about 1.3 molar equivalents of a t-butyl-halide compound to the dispersion, and
c. reacting the dispersion to form 4-t-butylpyrrole-2-carbaldehyde.

In yet another aspect, the instant invention provides a process for making a 4-tertiary-alkyl substituted pyrrole-2-carbaldehyde compound comprising:

a. reacting a pyrrole and a Vilsmeir reagent to produce a 2-substituted pyrrole compound; and
b. further reacting the 2-substituted pyrrole compound with an alkylating agent, in the presence of a catalyst; to form the 4-tertiary-alkyl substituted pyrrole-2-carbaldehyde compound.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION OF THE PREFERRED EMBODIMENTS

The present invention may be understood more readily by reference to the following detailed description of preferred embodiments of the invention and the Examples included therein and to the Figures and their previous and following description.

Before the present compounds, compositions and methods are disclosed and described, it is to be understood that this invention is not limited to specific synthetic methods, specific pharmaceutical carriers, or to particular pharmaceutical formulations or administration regimens, as such may, of course, vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "an aromatic compound" includes mixtures of aromatic compounds, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

In this specification and in the claims which follow, reference will be made to a number of terms which shall be defined to have the following meanings:

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

The term "alkyl" as used herein refers to a saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like. Preferred alkyl groups herein contain from 4 to 18 carbon atoms. The term "lower alkyl" intends an alkyl group of from one to six carbon atoms, preferably from one to four carbon atoms. The term "cycloalkyl" intends a cyclic alkyl group of from three to eight, preferably five or six carbon atoms. The term "substituted alkyl" as used herein refers to an alkyl group having one or more aromatic, heteroaromatic, or heteroatomic atoms or residues bonded thereto.

The term "aryl" denotes an aromatic ring radical containing 6 to 18 carbons that includes phenyl and naphthyl. The term "substituted aryl" denotes an aromatic radical as defined above that is substituted with one or more residues selected from alkyl, substituted alkyl, hydroxyl, cycloalkyl, amino, mono-substituted amino, di-substituted amino, acyloxy, nitro, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy or haloalkoxy, aryl, substituted aryl, heteroaryl, heterocyclic ring, substituted heterocyclic ring. The term "heteroaryl" denotes an aryl residue wherein at least one carbon of the aromatic ring radical is replaced with a heteroatom such as oxygen, nitrogen, sulfur, or the like.

The term "alkoxy" as used herein intends an alkyl group bound through a single, terminal ether linkage; that is, an "alkoxy" group may be defined as —OR where R is alkyl as defined above. A "lower alkoxy" group intends an alkoxy group containing from one to six, more preferably from one to four, carbon atoms.

The term "alkylene" as used herein refers to a difunctional saturated branched or unbranched hydrocarbon chain containing from 1 to 24 carbon atoms, and includes, for example, methylene (—CH$_2$—), ethylene (—CH$_2$—CH$_2$—), propylene (—CH$_2$—CH$_2$—CH$_2$—), 2-methylpropylene [—CH$_2$—CH(CH$_3$)—CH$_2$—], hexylene [—(CH$_2$)$_6$—] and the like. "Lower alkylene" refers to an alkylene group of from 1 to 6, more preferably from 1 to 4, carbon atoms. The term "cycloalkylene" as used herein refers to a cyclic alkylene group, typically a 5- or 6-membered ring.

The terms "alkene" or "olefin" as used herein intends a mono-unsaturated or di-unsaturated hydrocarbon group of 4 to 24 carbon atoms. Preferred groups within this class contain 4 to 18 carbon atoms. Asymmetric structures such as (AB)C=C(CD) are intended to include both the E and Z isomers. This may be presumed in structural formulae herein wherein an asymmetric alkene is present, or it may be explicitly indicated by the bond symbol—.

"Optional" or "optionally" means that the subsequently described event or circumstance may or may not occur, and that the description includes instances where said event or circumstance occurs and instances where it does not. For example, the phrase "optionally substituted lower alkyl" means that the lower alkyl group may or may not be substituted and that the description includes both unsubstituted lower alkyl and lower alkyl where there is substitution.

By the term "effective amount" of a compound or property as provided herein is meant such amount as is capable of performing the function of the compound or property for which an effective amount is expressed. As will be pointed out below, the exact amount required will vary from process to process, depending on recognized variables such as the compounds employed and the processing conditions observed. Thus, it is not possible to specify an exact "effective amount." However, an appropriate effective amount may be determined by one of ordinary skill in the art using only routine experimentation.

For the purposes of this disclosure, the word "pyrrole" may intend either the parent compound (C$_4$H$_5$N), or it may intend the genus of substituted compounds having pyrrole rings that are not part of a larger polycyclic aromatic fused ring systems.

In one aspect, the instant invention provides a process for making a 4-alkyl substituted pyrrole-2-carbaldehyde compound comprising reacting:

a. a pyrrole-2-carbaldehyde compound; and
b. an alkylating agent having at least four carbon atoms; in the presence of at least one catalyst; to form a 4-alkyl substituted pyrrole-2-carbaldehyde compound.

These processes for reacting pyrrole-2-carbaldehyde compounds with alkylating agents are, for the purposes of this disclosure, generally termed "alkylation reactions."

The pyrrole-2-carbaldehyde compounds have the general formula:

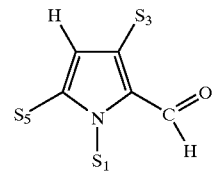

A single pyrrole-2-carbaldehyde compound may be employed as a starting material, or mixtures of two or more pyrrole-2-carbaldehyde compounds may also be employed. Generally, the substituent groups (S$_1$, S$_3$, and S$_5$) may be hydrogen, or any organic or inorganic substituent group which results in a reasonably chemically stable pyrrole-2-carbaldehyde compound. Examples of "S" groups bonded to the pyrrole ring via inorganic atoms include but are not limited to halogens such as flourine, chlorine, bromine, iodine, and groups derived therefrom; oxygen-containing residues such as hydroxy groups, alkoxy groups, carboxylate groups, and the like; sulfur containing groups such as thiols, thio-ethers, sulfates, sulfonates, and the like, nitrogen containing groups such as amino, nitro or nitroso groups. Preferably, the $S_3$ and/or $S_5$ substituent groups comprise "$R_x$" groups comprising hydrogen or carbon-containing groups; i.e., $R_3$ and/or $R_5$ groups. Carbon-containing $R_3$, and/or $R_5$ groups typically have from about 1 to about 18 carbon atoms. More preferably, the $R_3$ and/or $R_5$ substituent groups comprise from about 1 to about 12 carbon atoms. Preferably, the $S_1$, $S_3$, and/or $S_5$, groups, and/or $R_1$, $R_3$, and/or $R_5$ groups are not chemically bonded to each other, to form part of larger polycyclic ring systems.

The $S_1$ group bound to the nitrogen atom may comprise hydrogen, or a variety of organic or inorganic subsubstituent groups which form reasonably chemically stable bonds to the nitrogen atom of the pyrrole ring. In some embodiments, the $S_1$ substituent group may be an "N-protecting group" for the nitrogen atom. N-protecting groups are typically a group which is temporarily and/or removably bonded to the nitrogen atom, and which is present during the alkylation reactions, but then is subsequently removed from the nitrogen by chemical and/or physical methods, and replaced by hydrogen. Typical examples of N-protecting groups include alky or aryl sulfonyl groups, t-butoxycarbonyl groups, or any of the other N-protecting groups known to those skilled in the chemical arts. Because the introduction and removal of N-protecting groups typically adds chemical steps to the methods of the invention, and because such groups typically have an electron-withdrawing effect on the nitrogen atom and the pyrrole-2-carbaldehyde ring, which typically lowers and/alters reaction rates and selectivities, the use of N-protecting groups is within the scope of the invention, but are not generally favored embodiments.

Correspondingly, the 4-substituted pyrrole-2-carbaldehyde product compound or compounds produced by the processes of the invention have the structure:

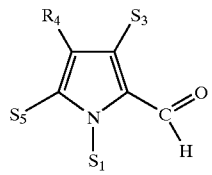

wherein $R_4$ is a carbon-containing group introduced by the alkylation reactions of the invention having four or more carbon atoms.

For example, can $R_4$ comprise a substituted or unsubstituted tertiary alkyl residue. Suitable tertiary alkyl $R_4$ residues include those having the structure:

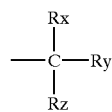

wherein Rx, Ry, and Rz are the same or different, and comprise at least one carbon atom. Preferably, Rx, Ry, and Rz comprise alkyl, substituted alkyl, aryl, substituted aryl, heteroaryl, or substituted heteroaryl residues.

$R_4$ groups comprise an organic residue, but the organic residue may additionally contain any organic or inorganic substituent residue or group which results in a reasonably chemically stable pyrrole-2-carbaldehyde compound. $R_4$ may contain aromatic or heteroaromatic residues, although the aromatic or heteroaromatic residues need not be directly bonded to the pyrrole ring. Preferred $R_4$ substituent groups include branched or unbranched, substituted or unsubstituted aliphatic or olefinic residues. Preferably, the $R_4$ substituent group comprises from about 4 to about 18 carbon atoms. More preferably, the $R_4$ substituent group comprises from about 4 to about 12 carbon atoms. Tertiary butyl groups, [—C—(CH$_3$)$_3$], (which may be alternatively termed "tert-butyl" or "t-butyl" groups), are the most preferred $R_4$ groups.

The pyrrole-2-carbaldehyde compounds used as reactants in the practice of the processes of the invention include:

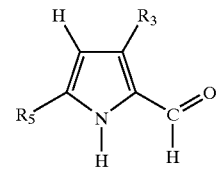

Preferably, the $R_3$ and/or $R_5$ residues independently comprise hydrogen, a halogen, an alkyl, an aromatic, or a heteroaromatic residue. Preferably, $R_3$ and/or $R_5$ comprise residues having from about 1 to about 25 carbon atoms. More preferably, $R_3$ and/or $R_5$ comprise residues having from about 2 to about 12 carbon atoms. Preferably, the $R_3$ and/or $R_5$ residues are not chemically reactive under the conditions of the subsequent acylation and/or alkylation reactions.

In certain embodiments of the invention, the pyrrole-2-carbaldehyde compound is reacted with an alkylating agent, in the course of an alkylation reaction to selectively form a 4-substituted pyrrole-2-carbaldehyde compound, which comprises

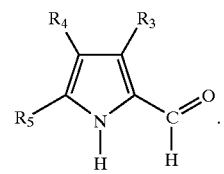

In many of these embodiments, $R_3$ $R_4$, and/or $R_5$ have the above-described structures. In preferred embodiments, $R_4$ comprises an alkyl, an alkylene, an olefinic, an aromatic, or a heteroaromatic residue. More preferably, the carbon atom of the $R_4$ group bonded to the pyrrole ring is an aliphatic carbon atom (as opposed to a carbon atom which is part of an unsaturated group or residue). $R_4$ groups comprising tertiary alkyl groups or residues are especially preferred in embodiments of the invention comprising alkylation reactions, and tertiary butyl groups are very highly preferred $R_4$ groups.

In one preferred embodiment of the invention, the pyrrole-2-carbaldehyde compound is

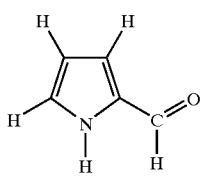

and the 4-substituted pyrrole-2-carbaldehyde compound formed therefrom is

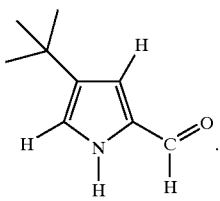

The processes of the invention employ at least one alkylating agent, which is the ultimate source of the substitutents at the 4-position, such as the $R_4$ residues. Suitable alkylating agents have a carbon-containing residue which is reactive in alkylation reactions, and have at least the number of carbon atoms described above for the $R_4$ substituent. The alkylation reactions of the invention frequently employ acidic catalysts, which typically react with the alkylating agent and/or the pyrrole-2-carbaldehydes, to generate small quantities of high energy intermediates, which produce the alkylated pyrrole-2-carbaldehyde compounds. Those of skill in the art are aware that the high energy intermediates involved are believed to be or be related to "carbonium ion" intermediates. Many alternative methods of generating such high energy "carbonium ion" intermediates both in the presence and absence of catalysts are known to those of skill in the art, and are within the scope of the present invention.

Typical classes of alkylating agents have a substituent which can be reacted to form the high energy carbonium ion intermediates. Typical classes of alkylating agents include an alkyl halide residue, an alcohol residue, or an olefin residue. Alkylating agents having alcohol residues may be employed with either Bronstead acid, or Lewis acid catalysts, and include alkylating agents in which the alcohol residue has been converted to a better "leaving group" by reaction with another chemical group, such as a carboxylic acid or sulfonate group. Preferred alkylating agents having an alcohol residue are tertiary butanol, tertiary butyl acetate, or methyl-tertiary butyl ether. Alkylating agents having an olefin residue, such as ethylene, propylene, 1-butene, cis or trans 2-butene, 1-hexene, and the like, may also be employed with either Bronstead acid, or a Lewis acid catalyst. A preferred alkylating agent having an olefin residue is isobutylene.

Alkylating agents comprising an alkyl halide residue are preferred, especially for alkylation reactions employing aluminum halide catalysts. The halide atoms of the alkyl halide residues include flourine, chlorine, bromine, and iodine. Suitable alkylating agents having an alkyl halide residue include, tertiary butyl chloride, tertiary butyl bromide, and tertiary butyl iodide. Alkylating agents having alkyl halide residues with more than four carbon atoms are suitable for the invention and include compounds such as 2-chloro-2-methylbutane, 1-bromo-1-methyl-1-phenylethane, 1,1,-dimethyl and the like. Those of skill in the art are aware that higher alkyl halides and the carbonium ion intermediates generated from them often undergo rearrangement reactions during the course of the alkylation reaction which can cause "migration" of organic groups such as methyl groups and aryl groups. For example, 2-chlorobutane may rearrange by the migration of a methyl group to yield a pyrrole product having predominantly tertiary butyl residues. Alkylating agents comprising an alkyl chloride residue are often less reactive than the analogous bromide or iodide compounds, but are sometimes preferred because alkyl chlorides are typically more available and/or less expensive than fluorides, bromides, or iodides. Tertiary butyl chloride is a very highly preferred alkylating agent.

It should be emphasized that the alkylating agent used in the above processes, which introduces a 4-alkyl substituent, need not be a t-butyl group. The alkylation agent may preferably be used to introduce a variety of branched or unbranched, or substituted or unsubstituted alkyl substituents, such as a 4-methyl, or a 4-ethyl substituent, onto the pyrrole, then the 4-alkylsubstituted-pyrrole-2-carbaldehyde could be further elaborated by a wide variety of subsequent chemical reactions, including t-butylation.

The processes of the invention employ catalysts for the alkylation reaction, which typically modify and/or activate the pyrrole and alkylating agents, and modify and/or control the rate and/ or selectivity of the alkylation reaction. The catalysts typically comprise "acidic" catalysts, which comprise Bronstead acid catalysts, Lewis acid catalysts, or mixtures thereof.

Bronstead acid catalysts are compounds which function by donating $H^+$ions to the substrates, or to the surrounding medium, which may or may not contain water. Bronstead acid catalysts are particularly suitable when alcohol or olefin alkylating agents are employed in the invention. Examples of Bronstead acid catalysts include but are not limited to mineral acids such as HF, HCl, HBr, HI, $H_2SO_4$, $HNO_3$, $H_3PO_4$, $HBF_4$ and the like, and strong "organic" acids such as methyl sulfonic acid, phenylsulfonic acid, toluenesulfonic acid, trifluoromethylsulfonic acid, sulfonated organic polymers or resins, and the like.

Lewis acid catalysts are preferred catalysts for the alkylation reactions of the invention, and generally comprise compounds having a reactive site or empty orbital which can accept electrons from a Lewis base compound. Well-known classes of compounds which function as Lewis acid catalysts include but are not limited to aluminum compounds, boron compounds, gallium compounds, antimony compounds, zinc compounds, zirconium compounds, tin compounds, solid inorganic acids, or a mixture thereof. Examples of known Lewis acid species include $AlBr_3$, $AlCl_3$, $GaCl_3$, FeCl3, $SbCl_5$, $ZnCl_2$, $ZrCl_4$, $SnCl_4$, $BCl_3$, $BF_3$, $SbCl_3$, alumina, silica, or a mixture thereof. Aluminum trichloride, $AlCl_3$, is a very highly preferred Lewis acid catalyst.

The quantity of catalyst utilized in the alkylation processes of the invention vary widely with the nature of the pyrrole-2-carbaldehyde substrate, the alkylating agent, the solvent, the temperature, the desired reaction rate and selectivity, and other variables. Although "catalysts" are often employed in a molar amount that is less than the amount of substrate, in the processes of the instant invention, the molar quantity of "catalyst" used may exceed the molar quantity of the reaction substates. Generally, the catalyst may be present in an amount from about 0.1 to about 5.0 moles per mole of pyrrole-2-carbaldehyde compound. Preferably, the catalyst is present in an amount from about 0.5 to about 3.0 moles per mole of pyrrole-2-carbaldehyde compound.

In alkylations of pyrrole-2-carbaldehyde compounds, it is sometimes observed that about one molar equivalent of catalyst initially complexes with the pyrrole-2-carbaldehyde compound, then a slight excess of catalyst over and above the first molar equivalent is needed to increase reaction rates to a desirable level. Therefore, in more preferred embodiments of the invention, the catalyst is present in an amount from about 1.0 to about 1.5 moles per mole of pyrrole-2-carbaldehyde compound. Even more preferably, the catalyst is present in an amount from about 1.01 to about 1.3 moles per mole of pyrrole-2-carbaldehyde compound.

The alkylation reactions of the processes of the invention need not, but often do occur in the presence of a solvent, or a mixture of solvents. Generally, the solvent is somewhat polar, so as to simultaneously dissolve polar acid catalysts and the organic substrates, while not being so polar or basic that the acid catalysts are effectively neutralized. Therefore, highly basic solvents such as amines are not preferred solvents. Preferably, the solvent is not decomposed by reaction with the catalyst or pyrrole-2-carbaldehyde compound. Therefore, solvents such as alcohols, many of which can react to form ethers in the presence of acids, are not typically preferred solvents. A preferred class of solvents include $C_1$–$C_2$ halogenated organic compounds or liquids. Examples of highly preferred solvent species are 1,2-dichloroethane or methylene chloride, or carbon disulfide.

The alkylation reactions of the invention occur over a broad range of temperatures, depending on the exact structures and concentrations of the pyrrole-2-carbaldehyde compounds, the alkylating agent, the catalyst, the solvent, the desired reaction rates and/or times, and various other factors. Generally, the temperature should be sufficiently high to produce completion of the alkylation reaction within about 48 hours, and low enough to avoid excessive self-condensation reactions of the pyrrole-2-carbaldehyde compounds, which are known to occur at elevated temperatures. Preferably, the alkylation reaction occurs at a temperature from about −20° C. to about 60° C. More preferably, the reaction occurs at a temperature from about −5° C. to about 30° C. Preferably, the reaction occurs within a time period from about 1 second to about 10 hours. More preferably, the reaction occurs in a time period from about 1 minute to about 5 hours. Most preferably, the reaction can occur in a time period from about 5 minutes to about 2 hours.

Isolation of the reaction product 4-substituted-pyrrole 2-carbaldehyde compounds are typically carried out by standard methods known to those of skill in the art. It is generally necessary to remove, recycle, neutralize, and/or decompose any acid catalysts utilized in the alkylation reaction. Neutralization and/or decomposition of the acid catalysts is typically accomplished by addition of water, hydroxylic compounds, or mineral or organic bases, and is generally accompanied by significantly exothermic reactions and/or liberation of heat. Therefore, the reaction vessel or apparatus is preferably adapted with mixing and/or heat transfer apparatus, so as to minimize local high temperatures during the alkylation reactions or isolation of the products, which can cause side reactions of the product aldehydes. Isolation of the product compounds is typically accomplished by standard means, such as extraction, distillation, crystallization, etc. Preferably, the 4-substituted-pyrrole 2-carbaldehyde compound is isolated by hydrolysis and extraction.

Optionally, the alkyl pyrrole-2-carbaldehydes produced by the processes of the invention (comprising various isomers and substitution patterns) may be hydrogenated, reduced with borohydride or aluminum hydride reagents, or otherwise reduced, to form variously substituted alkyl 2-hydroxymethyl pyrrole compounds. For example:

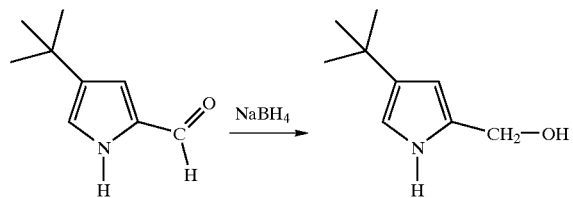

The variously substituted pyrrole-2-carbaldehyde utilized in processes of the invention as starting materials can be prepared by any of the methods known to those of skill in the art. Those methods may vary, depending on the desired pattern of substituents at the 1-, 3-, and 5-positions of the pyrrole-2-carbaldehyde. For example, as described above, Mueller-Westerhoff and Sweigers prepared 5-t-butyl-pyrrole-2-carbaldehyde by reacting pyrrole with a Vilsmeir reagent, then alkylating the iminium salt intermediate with t-butyl chloride and aluminum chloride. Reaction of pyrroles with Vilsmeier reagents is a preferred method of synthesizing many 3- or 5-substituted pyrrole-2-carbaldehyde compounds. A preferred method of preparing pyrrole-2-carbaldehyde (the parent compound, $C_5H_5ON$) comprises reacting pyrrole ($C_4H_5N$) with a Vilsmeir reagent.

Vilsmeir reagents are generally prepared by reacting an N,N-dialkylamide (such as dimethylformamide) and a condensation and/or dehydration reagent. While a variety of condensation and/or dehydration reagents suitable for the preparation of Vilsmeir reagents are known in the art, oxalyl chloride, $POCl_3$, or phosgene are preferred condensation reagents. Hence, in a preferred embodiment of the instant process, the pyrrole-2-carbaldehydes are prepared by reacting pyrrole with an N,N-dialkylformamide and a condensation reagent.

In one aspect, the invention provides a two-step method for making a 4-tertiary-alkyl substituted pyrrole-2-carbaldehyde compound comprising:

a. reacting a pyrrole and a Vilsmeir reagent to produce a 2-substituted pyrrole compound; and b. further reacting the 2-substituted pyrrole compound with an alkylating agent, in the presence of a catalyst; to form the 4-tertiary-alkyl substituted pyrrole-2-carbaldehyde compound.

In general, the starting pyrrole of this two-step process may have any of the S or R substitutents described hereinabove at it's 1-, 3-, or 5-positions, but it must have hydrogen at it's 2- or 4-positions. It should be noted that the alkylating agent used in the above process, which results in 4-substituent need not be a t-butyl group. The alkylation agent of this two-step process may preferably be used to introduce a variety of alkyl substituents, including a 4-methyl, or a 4-ethyl substituent onto the pyrrole, then the 4-methyl-pyrrole-2-carbaldehyde or the 4-ethyl-pyrrole-2-carbaldehydes could be further elaborated by a wide variety of subsequent chemical reactions, including t-butylation.

An example of a two step process is shown by the following chemical equation:

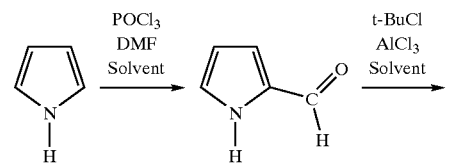

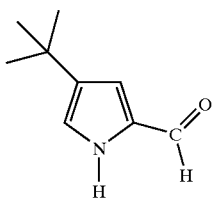

In certain embodiments of the two-step process, the further reacting occurs without isolation of the 2-substituted pyrrole compound, which is an intermediate in the two-step process. In preferred embodiments, the unisolated intermediate 2-substituted pyrrole compound comprises

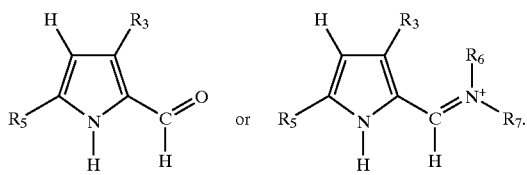

It is to be understood that the cationic iminium compound illustrated above is typically the first-formed product of a Vilsmeir reaction, but that the cationic iminium compound might be hydrolyzed to form the illustrated pyrrole-2-carbaldehyde, without actual isolation of either compound, prior to further reacting with an alkylating agent.

Preferably, the $R_3$ and/or $R_5$ substituents of the unisolated intermediates illustrated above may independently comprise hydrogen, an alkyl, an aromatic, a heteroaromatic, an alkoxy, a thio, a carboxyllic acid or ester, an acyl, an amino, a nitro, or a halogen residue; and the $R_6$ and/or $R_7$ substituents of the cationic iminium compound may independently comprise an alkyl, an alkylene, an aromatic, or a heterocyclic residue.

In another aspect, the instant invention provides a process for making 4-t-butyl-pyrrole-2-carbaldehyde, comprising:
  a. dispersing pyrrole-2-carbaldehyde and from about 1.0 to about 1.5 molar equivalents of $AlCl_3$ in a solvent:
  b. adding from about 0.8 to about 1.3 molar equivalents of t-butyl-chloride to the dispersion, and
  c. reacting the dispersion at a suitable temperature and for a time sufficient to form 4-t-butyl-pyrrole-2-carbaldehyde.

Optionally, a 4-t-butyl-pyrrole-2-carbaldehyde produced by this preferred process may be hydrogenated, reduced with borohydride or aluminum hydride reagents, or otherwise reduced, to form 4-t-butyl-2-hydroxymethyl pyrrole.

In yet another aspect, the invention provides the products produced by the process of the invention. In particular, the invention provides 4-t-butyl-2-hydroxymethyl pyrrole produced by the processes of the invention.

The compounds of the invention may be readily synthesized using techniques generally known to synthetic organic chemists. Suitable experimental methods for making and derivatizing aromatic compounds are described, for example, in the references cited in the Background section herein above, the disclosures of which are hereby incorporated by reference for their general teachings and for their synthesis teachings. Methods for making specific and preferred compounds of the present invention are described in detail in Examples 1–9 below.

EXPERIMENTAL

The following examples are put forth so as to provide those of ordinary skill in the art with a complete disclosure and description of how the compounds claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at room temperature, and pressure is at or near atmospheric.

EXAMPLE 1

Reaction of Pyrrole-2-carboxaldehyde with t-butyl Chloride in the Presence of $AlCl_3$ (0.2 equiv) in 1, 2-dichloroethane To a suspension of $AlCl_3$ (49 mg, 0.4 mmol, 0.2 equiv) in 1,2-dichloroethane (5 mL) was added pyrrole-2-carboxaldehyde (190 mg, 2 mmol, 1.0 equiv) at room temperature, resulting a pink suspension. The flask was equipped with an ice bath, and t-butyl chloride (226 mg, 2.4 mmol, 1.2 equiv) was added via syringe dropwise at 0° C. over 1 min. The mixture was then stirred at 0° C. for 3 min and at room temperature for 20 min. GC-MS showed only the starting material, without the formation of the t-butyl chloride derived side-products. Stirring further for 6 h at room temperature did not give any products and side-products. Only the starting material was observed. This example illustrates that the desired product may not form in a suitable reaction time in the absence of sufficient catalyst.

EXAMPLE 2

Reaction of Pyrrole-2-carboxaldehyde with t-butyl Chloride in the Presence of $AlCl_3$ (0.5 equiv) in 1, 2-dichloroethane To a suspension of $AlCl_3$ (133 mg, I mmol, 0.5 equiv) in 1,2-dichloroethane (5 mL) was added pyrrole-2-carboxaldehyde (190 mg, 2 mmol, 1.0 equiv) at room temperature, resulting a red solution. The flask was equipped with ice bath, and t-butyl chloride (229 mg, ca. 2.4 mmol, 1.2 equiv) was added via syringe dropwise at 0° C. over 1 min. The mixture was stirred at 0° C. for 5 min and at room temperature for 4h. GC-MS showed only the starting material. This example illustrates that the desired product may not form in a suitable reaction time in the absence of sufficient catalyst.

EXAMPLE 3

Reaction of Pyrrole-2-carboxaldehyde with t-butyl Chloride in the Presence of $AlCl_3$ (0.8 equiv) in 1, 2-dichloroethane To a suspension of $AlCl_3$ (213 mg, 1.6 mmol, 0.8 equiv) in 1,2-dichloroethane (5 mL) was added pyrrole-2-carboxaldehyde (190 mg, 2 mmol, 1.0 equiv) at room temperature, resulting a slightly red suspension. The flask was equipped with an ice bath, and t-butyl chloride (229 mg, ca. 2.4 mmol, 1.2 equiv) was added via syringe dropwise at 0° C. over 1 min. The mixture was stirred at 0° C. for 5 min and at room temperature for 6.5 h. GC-MS showed only the starting material. This example illustrates that the desired product may not form in a suitable reaction time in the absence of sufficient catalyst.

EXAMPLE 4

Reaction of Pyrrole-2-carboxaldehyde with t-butyl Chloride in the Presence of $AlCl_3$ (1.2 equiv) in 1, 2-dichloroethane To a suspension of $AlCl_3$ (320 mg, 2.4 mmol, 1.2 equiv) in 1,2-dichloroethane (5 mL) was added pyrrole-2- carboxaldehyde (190 mg, 2 mmol, 1.0 equiv) at room temperature. The flask was equipped with an ice bath, and t-butyl chloride (223 mg, 2.4 mmol, 1.2 equiv) was added via syringe dropwise at 0° C. over 1 min (no gas protection). The mixture was then stirred at 0° C. for 3 min and at room temperature for 1.5 h. GC-MS indicated the complete consumption of the starting material and the formation of mono-t-butyl-pyrrole-2-carboxaldehyde quantitatively. The solvent was evaporated, and the residue was dissolved in water (10 mL) and 5% HCl (30 mL) and extracted with diethyl ether (60+60+20 mL) (colorless solution). The organic solution was dried with $MgSO_4$. Removal of the solvent afforded pink solid. The latter was dissolved in $NaHCO_3$ (25 mL) (colorless solution) and extracted with dichloromethane (40+20 mL) (yellow solution). The dichloromethane solution was dried with $MgSO_4$, and removal of the solvent furnished a slightly pink solid (287 mg, 95%) as nearly pure 4-t-butylpyrrole-2-carboxaldehyde as determined by NMR. Melting point 82–83° C. (hexanes); IR (KBr pellet, $cm^{-1}$): 3243 (s), 2956 (s), 2863 (m), 1660 (s), 1490 (m), 1449 (m), 1449 (m), 1387 (s), 1353 (s), 1238 (m), 1141 (s), 1106 (m), 955 (s), 841 (s), 764 (s), 662 (s), $^1H$ NMR ($CDCl_3$, 400 MHZ): δ 1.27 (s, 9 H), 6.89–6.90 (m, 1 H), 6.99 (app pent, J=1.5 Hz, 1 H), 9.44 (d, J=1.1 Hz 9.50–9.70(brs, 1 H). $^{13}CNMR(CDCl_3$, 100 MHZ): δ 179.2, 138.5, 132.4, 123.1, 119.0, 31.6, 30.5. This example illustrates that good yields of desired products may be obtained on small scales and in short reaction times, if more than one molar equivalent of $AlCl_3$ catalyst per mole of pyrrole-2-carbaldehyde is employed.

EXAMPLE 5

Reaction of Pyrrole-2-carboxaldehyde with t-butyl Chloride in the Presence of $AlCl_3$ (1.2 equiv) in 1,2-dichloroethane To a suspension of $AlCl_3$ (320 mg, 2.4 mmol, 1.2 equiv) in 1,2-dichloroethane (5 mL) was added pyrrole-2-carboxaldehyde (189.9 mg, 2 mmol, 1.0 equiv) at room temperature, resulting a yellow solution exothermically. The flask was equipped with an ice bath, and t-butyl chloride (225 mg, 2.4 mmol, 1.2 equiv) was added via syringe dropwise at 0° C. over 1 min. The mixture was then stirred at 0° C. for 3 min and at room temperature for 20 min. GC-MS indicated the complete consumption of the starting material and the formation of mono-t-butyl-pyrrole-2-carboxaldehyde quantitatively. The solvent was evaporated, and the residue was dissolved in EtOAc (40 mL), washed with water (30 mL) and $NaHCO_3$ (15 mL) (slightly white cloudy), and dried with $MgSO_4$. Removal of the solvent furnished a slightly pink (most white) solid (293 mg, 97%) as pure 4-t-butylpyrrole-2-carboxaldehyde, as determined by NMR. This example illustrates that good yields of desired products may be obtained on small scales and in short reaction times, if significantly more than one molar equivalent of $AlCl_3$ catalyst per mole of pyrrole-2-carbaldehyde is employed.

EXAMPLE 6

Reaction of Pyrrole-2-carboxaldehyde with t-butyl Chloride in the Presence of $AlCl_3$ (1.2 equiv) in 1,2-dichloroethane To a suspension of $AlCl_3$ (800 mg, 6 mmol, 1.2 equiv) in 1,2-dichloroethane (1 mL) was added pyrrole-2-carboxaldehyde (475 mg, 5 mmol, 1.0 equiv) at 0° C. It remained as suspension; therefore, the ice bath was removed. After 10 min (still some solid suspended in a greenish solution), the flask was equipped with an ice bath, and t-butyl chloride (550 mg, ca. 6 mmol, 1.2 equiv) was added via syringe dropwise at 0° C. over 3 min. The mixture was then stirred at 0° C. for 5 min and at room temperature for 7 min. GC-MS indicated the complete consumption of the starting material and the formation of mono-t-butyl-pyrrole-2-carboxaldehyde quantitatively. The solvent was evaporated, and the residue was dissolved in EtOAc (80 mL), washed with water (50 mL) and $NaHCO_3$ (50 mL) (slightly white cloudy) (organic phase: orange yellow solution), and dried with $MgSO_4$. Removal of the solvent furnished a brownish solid (820 mg, theory: 756 mg) containing a single product, 4-t-butylpyrrole-2-carboxaldehyde, as determined by NMR. This example illustrates that good yields of desired products may be obtained on somewhat larger scales and in short reaction times, if more than one molar equivalent of $AlCl_3$ catalyst per mole of pyrrole-2-carbaldehyde is employed.

EXAMPLE 7

Reaction of Pyrrole-2-carboxaldehyde (10 mmol) with t-butyl Chloride in the Presence of $AlCl_3$ (1.2 equiv) in 1,2-dichloroethane To a suspension of $AlCl_3$ (1.6 g, 12 mmol, 1.2 equiv) in 1,2-dichloroethane (2 mL) was added pyrrole-2-carboxaldehyde (951 mg, 10 mmol, 1.0 equiv). It changed to a dark greenish solution immediately exothermically. The flask was equipped with an ice bath, and t-butyl chloride (1.205 g, ca. 13 mmol, 1.3 equiv) was added via syringe dropwise at 0° C. over 5 min. The mixture was then stirred at room temperature for 35 min. GC-MS showed the complete consumption of the starting material and formation of mono-t-butyl-pyrrole-2-carboxaldehyde along with 4 minor by-products including the corresponding di-t-butylation product in 82:10:6:2:trace ratio (in the order of the retention time). After stirring at room temperature for 45 min, the solvent was evaporated, and the residue was dissolved in EtOAc (80 mL), washed with water (80 mL) and $NaHCO_3$ (40 mL) (slightly white cloudy), and dried with $MgSO_4$. Removal of the solvent furnished a brown solid (1.648 g, theory: 1.512 g) containing 4-t-butylpyrrole-2-carboxaldehyde as a single product, along with traces of impurities. This example illustrates that good yields of desired products may be obtained on yet larger scales and in short reaction times, if more than one molar equivalent of $AlCl_3$ catalyst per mole of pyrrole-2-carbaldehyde is employed.

EXAMPLE 8

Reaction of Pyrrole-2-carboxaldehyde (100 mmol) with t-butyl Chloride (1.2 equiv) in the Presence of $AlCl_3$ (1.12 equiv) in 1,2-dichloroethane (10 mL)

To a suspension of $AlCl_3$ (14.95 g, 112 mmol, 1.12 equiv) in 1,2-dichloroethane (10 mL) was added pyrrole-2-carboxaldehyde (9.51 g, 100 mmol, 1.0 equiv) (100 mL flask was equipped with a regular water bath). It changed to a dark greenish solution highly exothermically. (After stirring for 12 min, GC-MS showed no change of the starting material.) After stirring for 8 min, the flask was equipped with an ice bath, and t-butyl chloride (11.1 g, 120 mmol, 1.2 equiv) was added via syringe dropwise at 0° C. over 35 min. The mixture was further stirred at 0° C. 5 min. GC-MS showed the complete consumption of the starting material and formation of mono-t-butyl-pyrrole-2-carboxaldehyde along with 3 minor by-products including the corresponding di-t-butylation product in 92:1:4:1 ratio (in the order of the retention time). After further stirring at 0° C. for 10 min, the solvent was evaporated, and the residue was dissolved in EtOAc (160 mL), washed with ice (changing into 220 mL water) and NaHCO$_3$ (150+75 mL), and dried with MgSO$_4$. Removal of the solvent furnished a brownish yellow solid (18.028 g, theory: 15.12 g) containing 4-t-butylpyrrole-2-carboxaldehyde as a single product along with some solvent EtOAc. The crude product was directly for porphyrin synthesis. This example illustrates that good yields of desired products may be obtained on yet larger scales and in short reaction times, if more than one molar equivalent of AlCl$_3$ catalyst per mole of pyrrole-2-carbaldehyde is employed.

EXAMPLE 9

One Pot Reaction of Pyrrole with a Vilsmeier Reagent, Followed by Reaction with t-butyl Chloride in the Presence of AlCl$_3$ Oxalyl chloride (0.44 mL, ca. 635 mg, 5 mmol, 1 equiv) was added via syringe into a solution of the dimethyl formamide (DMF) (370 mg, ca. 5 mmol, 1 equiv) in 1,2-dichloroethane (10 mL) at 0° C. under nitrogen over 10 min. The mixture was then stirred at room temperature under nitrogen for 20 min. The flask was equipped with an ice bath again, and to the resultant white suspension was added pyrrole (334 mg, 5 mmol, 1 equiv) with 1,2-dichloroethane (5 mL) via syringe over 5 min, resulting a clear yellow solution. After stirring at room temperature for 30 min, AlCl$_3$ (1.46 g, 11 mmol, 2.2 equiv) was added followed by t-butyl chloride (0.65 mL, ca. 555 mg, 1.2 equiv) at room temperature under nitrogen. After stirring at room temperature for 2 h, the reaction mixture was equipped with ice bath, and 5 mL of 4N NaOH solution along with 20 mL of water were added. After stirring at room temperature for 10 min, the reaction mixture was diluted with 4N NaOH solution (30 mL) and extracted with dichloromethane (80+70 mL). The organic solution was dried with MgSO$_4$, and removal of the solvent afforded a red liquid (0.814 g), which contained the desired product 4-t-butyl-pyrrole-2-carboxaldehyde and some other unidentified products, as determined by NMR. This example illustrates a two-step, "one pot" process for making 4-t-butyl-pyrrole-2-carboxaldehyde from pyrrole.

Throughout this application, various publications are referenced. The disclosures of these publications in their entireties are hereby incorporated by reference into this application in order to more fully describe the state of the art to which this invention pertains.

It will be apparent to those skilled in the art that various modifications, substitutions, omissions, and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A process for making a 4-alkyl substituted pyrrole-2-carbaldehyde compound comprising reacting:
   a. a pyrrole-2-carbaldehyde compound prepared by reacting a pyrrole compound with a Vilsmeir reagent; and
   b. an alkylating agent having at least four carbon atoms; in the presence of at least one catalyst; to form a 4-alkyl substituted pyrrole-2-carbaldehyde compound.

2. The process of claim 1, wherein the pyrrole-2-carbaldelyde compound has the structure

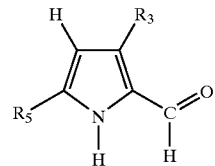

wherein R$_3$ and R$_5$ are independently hydrogen, a halogen, an alkyl, a substituted alkyl, an aromatic, or a heteroaromatic group.

3. The process of claim 1, wherein the pyrrole-2-carbaldehyde compound is

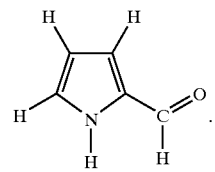

4. The process of claim 1, wherein the 4-substituted pyrrole-2-carbaldehyde compound has the structure

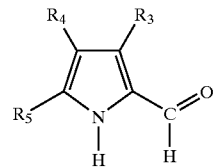

wherein R$_3$ and R$_5$ are independently hydrogen, a halogen, an alkyl, a substituted alkyl, an aromatic, or a heteroaromatic group; and R$_4$ is a substituted or unsubstituted tertiary alkyl group having four or more carbon atoms.

5. The process of claim 4, wherein the tertiary alkyl R$_4$ group has the structure:

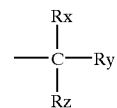

wherein R$_x$, R$_y$, and R$_z$ are the same or different, and each comprises at least one carbon atom.

6. The process of claim 5, wherein R$_x$, R$_y$, and R$_z$ are an alkyl, substituted alkyl, aryl, substitated aryl, heteroaryl, or substituted heteroaryl group.

7. The process of claim 5, wherein R$_x$, R$_y$, and R$_z$ are —CH$_3$ groups.

8. The process of claim 1, wherein the 4-tertiary-alkyl substituted pyrrole-2-carbaldehyde compound is

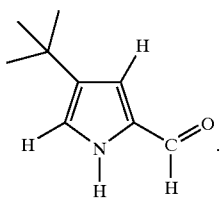

9. The process of claim 5, wherein the alkylating agent comprises a $C_4$–$C_{18}$ compound that reacts and/or rearranges in the presence of the catalyst to introduce the tertiary alkyl $R_4$ residue into the 4 position of the pyrrole-2-carbaldehyde compound.

10. The process of claim 1, wherein the aylkylating agent is an alkyl halide, an alcohol, or an olefin.

11. The process of claim 1, wherein the alkylating agent is a tertiary butyl halide.

12. The process of claim 1, wherein the alkylating agent is tertiary butyl chloride.

13. The process of claim 1, wherein the alkylating agent is tertiary butanol.

14. The process of claim 1, wherein the alkylating agent is an olefin, and the catalyst is a Bronstead acid.

15. The process of claim 1, wherein the catalyst is present in an amount equal to or greater than about 1.0 moles per mole of pyrrole-2-carbaldehyde compound.

16. The process of claim 1, wherein the catalyst is present in an amount from about 1.01 to about 1.3 moles per mole of pyrrole-2-carbaldehyde compound.

17. The process of claim 1, wherein the catalyst comprises a Lewis acid.

18. The process of claim 1, wherein the catalyst comprises an aluminum compound, a boron compound, a gallium compound, an antimony compound, a zinc compound, a zirconium compound, a tin compound, or a mixture thereof.

19. The process of claim 1, wherein the catalyst comprises $AlBr_3$, $AlCl_3$, $GaCl_3$, $FeCl_3$, $SbCl_5$, $ZnCl_2$, $ZrCl_4$, $SnCl_4$, $BCl_3$, $BF_3$, or $SbCl_3$.

20. The process of claim 1, wherein the catalyst is $AlCl_3$.

21. The process of claim 1, wherein the catalyst is a Bronstead acid catalyst.

22. A process for making 4-t-butyl-pyrrole-2-carbaldehyde compound comprising:

a. dispersing pyrrole-2-carbaldehyde prepared by reacting a pyrrole compound with a Vilsmeir reagent and from about 1.0 to about 1.5 molar equivalents of $AlCl_3$ in a solvent:

b. adding from about 0.8 to about 1.3 molar equivalents of a t-butyl-halide compound to the dispersion, and c. reacting the dispersion to form 4-t-butylpyrrole-2-carbaldehyde.

* * * * *

UNITED STATES PATENT AND TRADEMARK OFFICE
CERTIFICATE OF CORRECTION

PATENT NO. : 6,441,194 B1
DATED : August 27, 2002
INVENTOR(S) : Liebeskind et al.

It is certified that error appears in the above-identified patent and that said Letters Patent is hereby corrected as shown below:

Column 19,
Line 16, please correct the spelling of the word "aylkylating" to read -- alkylating --

Signed and Sealed this

Fourteenth Day of January, 2003

JAMES E. ROGAN
*Director of the United States Patent and Trademark Office*